United States Patent
Abenaim

(10) Patent No.: US 8,942,342 B2
(45) Date of Patent: Jan. 27, 2015

(54) MULTI-MODALITY IMAGE ACQUISITION

(75) Inventor: Daniel Abenaim, Lynnfield, MA (US)

(73) Assignee: Analogic Corporation, Peabody, MA (US)

( * ) Notice: Subject to any disclaimer, the term of this patent is extended or adjusted under 35 U.S.C. 154(b) by 100 days.

(21) Appl. No.: 12/345,080

(22) Filed: Dec. 29, 2008

(65) Prior Publication Data

US 2010/0166147 A1      Jul. 1, 2010

(51) Int. Cl.
*A61B 6/04* (2006.01)
*A61B 8/00* (2006.01)
*A61B 6/00* (2006.01)
*A61B 8/08* (2006.01)

(52) U.S. Cl.
CPC ............. *A61B 8/4416* (2013.01); *A61B 6/502* (2013.01); *A61B 6/5247* (2013.01); *A61B 8/0825* (2013.01); *A61B 6/4417* (2013.01); *A61B 6/5235* (2013.01)
USPC ................................ 378/37; 378/63; 600/437

(58) Field of Classification Search
CPC .............................. A61B 6/502; A61B 8/0825
USPC ............................ 378/21, 22, 37, 63; 600/437
See application file for complete search history.

(56) References Cited

U.S. PATENT DOCUMENTS

| | | | |
|---|---|---|---|
| 4,478,084 A * | 10/1984 | Hassler et al. ................... | 73/620 |
| 5,868,673 A * | 2/1999 | Vesely ........................... | 600/461 |
| 5,938,613 A * | 8/1999 | Shmulewitz .................. | 600/461 |
| 6,385,474 B1 | 5/2002 | Rather et al. | |
| 6,396,940 B1 | 5/2002 | Carrott et al. | |
| 6,450,960 B1 | 9/2002 | Rather et al. | |
| 6,540,678 B2 | 4/2003 | Rather et al. | |
| 6,607,489 B2 | 8/2003 | Hoctor et al. | |
| 6,672,165 B2 | 1/2004 | Rather et al. | |
| 6,728,567 B2 | 4/2004 | Rather et al. | |
| 6,837,854 B2 | 1/2005 | Moore et al. | |
| 6,926,672 B2 | 8/2005 | Moore et al. | |
| 6,984,210 B2 | 1/2006 | Chambers et al. | |
| 7,285,092 B2 | 10/2007 | Duric et al. | |
| 2002/0099290 A1 * | 7/2002 | Haddad ......................... | 600/443 |

(Continued)

FOREIGN PATENT DOCUMENTS

| EP | 1977692 A2 | 8/2008 |
|---|---|---|
| WO | 0009014 | 2/2000 |

OTHER PUBLICATIONS

Yang; et al., "Stationary digital breast tomosynthesis system with a multi-beam field emission x-ray source array", Medical Imaging 2008: Physics of Medical Imaging, edited by Jiang Hsieh, Ehsan Samei, Proc. of SPIE vol. 69t3, 69131A, (2008) 1605-7422/08.

(Continued)

*Primary Examiner* — Glen Kao
(74) *Attorney, Agent, or Firm* — Cooper Legal Group LLC

(57) ABSTRACT

The techniques described herein provide a means for generating an x-ray image and ultrasound image depicting parallel planes of an object under examination and may be used in conjunctions with x-ray or ultrasound techniques known to those in the field (e.g., x-ray tomosynthesis, computed tomography ultrasound imaging, etc.). In one example, one or more x-ray images are spatially coincident to one or more ultrasound images and the images may be combined through spatial registration. It finds particular application to mammography examinations but may be used in other fields that use information from multiple modalities.

6 Claims, 5 Drawing Sheets

(56) References Cited

U.S. PATENT DOCUMENTS

| | | |
|---|---|---|
| 2003/0007598 A1* | 1/2003 | Wang et al. ............ 378/37 |
| 2003/0072417 A1* | 4/2003 | Kaufhold et al. ............ 378/37 |
| 2003/0167004 A1* | 9/2003 | Dines et al. ............ 600/437 |
| 2004/0030227 A1 | 2/2004 | Littrup et al. |
| 2004/0068170 A1* | 4/2004 | Wang et al. ............ 378/37 |
| 2004/0249271 A1* | 12/2004 | Besson et al. ............ 378/37 |
| 2005/0089205 A1 | 4/2005 | Kapur |
| 2005/0100129 A1* | 5/2005 | McKenna ............ 378/37 |
| 2005/0288581 A1 | 12/2005 | Kapur |
| 2006/0173304 A1* | 8/2006 | Wang ............ 600/437 |
| 2007/0003117 A1* | 1/2007 | Wheeler et al. ............ 382/128 |
| 2007/0156047 A1* | 7/2007 | Nagler et al. ............ 600/436 |
| 2008/0045833 A1* | 2/2008 | Defreitas et al. ............ 600/429 |
| 2008/0101530 A1* | 5/2008 | Ullberg et al. ............ 378/4 |
| 2008/0234578 A1 | 9/2008 | Claus |
| 2009/0175408 A1* | 7/2009 | Goodsitt et al. ............ 378/37 |
| 2009/0290679 A1 | 11/2009 | Mikami et al. |
| 2009/0316854 A1* | 12/2009 | Ismail et al. ............ 378/4 |
| 2010/0111379 A1* | 5/2010 | Suri et al. ............ 382/128 |
| 2010/0166147 A1 | 7/2010 | Abenaim |

OTHER PUBLICATIONS

International Search Report and Written Opinion cited in related application No. PCT/US2010/056855 dated Jul. 27, 2011.

Non-Final Office Action cited in related U.S. Appl. No. 12/978,728 dated Sep. 26, 2011.

Response to Non-Final Office Action cited in related U.S. Appl. No. 12/978,728 dated Dec. 27, 2011.

Final Office Action cited in related application No. 12/978,728 dated May 14, 2012.

\* cited by examiner

MULTI-MODALITY IMAGE ACQUISITION

BACKGROUND

The present application relates to the examination of objects using different image acquisition modalities. It finds particular application to the use of ultrasound and x-rays in mammography examinations. It also relates to medical and other applications where information from multiple imaging modalities can be used to provide additional information about the structure and/or function of an object.

X-ray devices, in general, generate one or more 2-D images of an object under examination. The object is exposed to radiation, and an image is formed based upon the radiation absorbed by the object, or rather an amount of radiation that is able to pass through the object. Highly dense objects absorb more radiation than less dense objects, and thus an object having a higher density, such as a bone or mass, for example, will be apparent when surrounded by less dense objects, such as fat tissue or muscle.

In medical systems, x-ray devices are commonly used to detect broken bones, masses, calcium deposits, etc. that are not visible to the naked eye. One type of x-ray device is a mammography unit that generally comprises an x-ray tube, two compression paddles, and a detector array. The detector array and one compression paddle are mounted on a diametrically opposing side of the breast tissue (e.g., the object under examination) from the x-ray tube and the second compression paddle. The x-ray tube emits x-rays, and the x-rays traverse the breast tissue, while it is compressed between the two paddles. X-rays that traverse the breast tissue are detected by the detector array. In digital radiology, digital detectors (of the detector array) detect the x-rays, and reconstruction algorithms are used to create one or more two-dimensional (2-D) images of the breast tissue in the latitudinal dimension (e.g., orthogonal to a center x-ray beam and/or parallel to the detector array).

While 2-D x-ray images are useful in mammography and other applications, these images provide little or no resolution in the longitudinal direction (e.g., parallel to the x-ray beam and/or orthogonal to the detector plane formed by the detectors). On a breast examination, for example, a 2-D image cannot provide information about whether a mass is nearer the x-ray tube or the detector array. A less dense, but potentially cancerous mass, for example, may be masked by a more dense target, such as scar tissue, if the mass and scar tissue have a similar latitudinal coordinate (e.g., one target is on top of the other). Additionally, many (e.g., 85 percent in breast cancer screenings) positive findings are false positives (e.g., are not related to breast cancer). Therefore, patients are ordinarily called back for further testing if a positive finding is detected.

Ultrasound imaging is one common method used to confirm or reject an initial positive finding. Typically, an ultrasound probe transmits high-frequency sound waves (e.g., pulses) into the object under examination. As the sound waves travel through the object, some of the sound waves interact with a more dense target (e.g., mass, scar tissue, etc.), for example, that reflects a larger number of sound waves and/or causes a more significant attenuation of the sound waves (relative to less dense targets within the object). The sound waves that are reflected (e.g., echoes) are detected by the probe, and an ultrasound device calculates the distance from the probe to the more dense object and/or the intensity of the echoes. An image of the target inside the breast is formed based upon the calculations.

While current cancer screening techniques have proven effective for detecting early signs of cancer in some situations, there remains room for improvement. The x-ray scanning and ultrasound imaging are typically done at different times and in different physical positions. For example, in breast cancer screening, the mammography exam is usually done with a woman standing up and the breast tissue in a compressed state, while the ultrasound exam is done with the woman flat on her back and the breast stretched out (e.g., to reduce the distance the sound wave has to travel in the breast, thereby improving the image quality). Therefore, it is difficult to compare the images and detect similar details in the x-ray and the ultrasound images. Additionally, initial false positives can generate feelings of anxiety or distress that can last well after the ultrasound confirms that the initial positive finding was false.

SUMMARY

Aspects of the present application address the above matters, and others. According to one aspect, a scanner comprises an x-ray source configured to emit x-rays into an examination region of the scanner, and a detector configured to detect x-rays emitted into the examination region that have traversed an object under examination situated therein, the detected x-rays used to generate an x-ray image depicting a first plane of the object. The scanner also comprises an ultrasound imaging apparatus configured to generate an ultrasound image of a second plane of the object that is substantially parallel to the first plane.

According to another aspect, a method of acquiring data from two scanning modalities regarding an object under examination is provided. The method comprises acquiring data related to an x-ray image and data related to an ultrasound image of the object under examination such that a resulting ultrasound image depicts a plane of the object that is substantially parallel with a plane of the object depicted in a resulting x-ray image.

According to yet another aspect, a method of acquiring data for spatial registration is provided. The method comprises detecting x-rays that traverse an object under examination and generating an x-ray image of a plane of the object based upon the detected x-rays. The method also comprises emitting sound waves into the object, the sound waves interacting with the object in a plane that is substantially parallel to the plane depicted in the x-ray image. The method further comprises detecting sound waves that interact with the object in the plane that is substantially parallel to the plane depicted in the x-ray image.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

Figure 1:
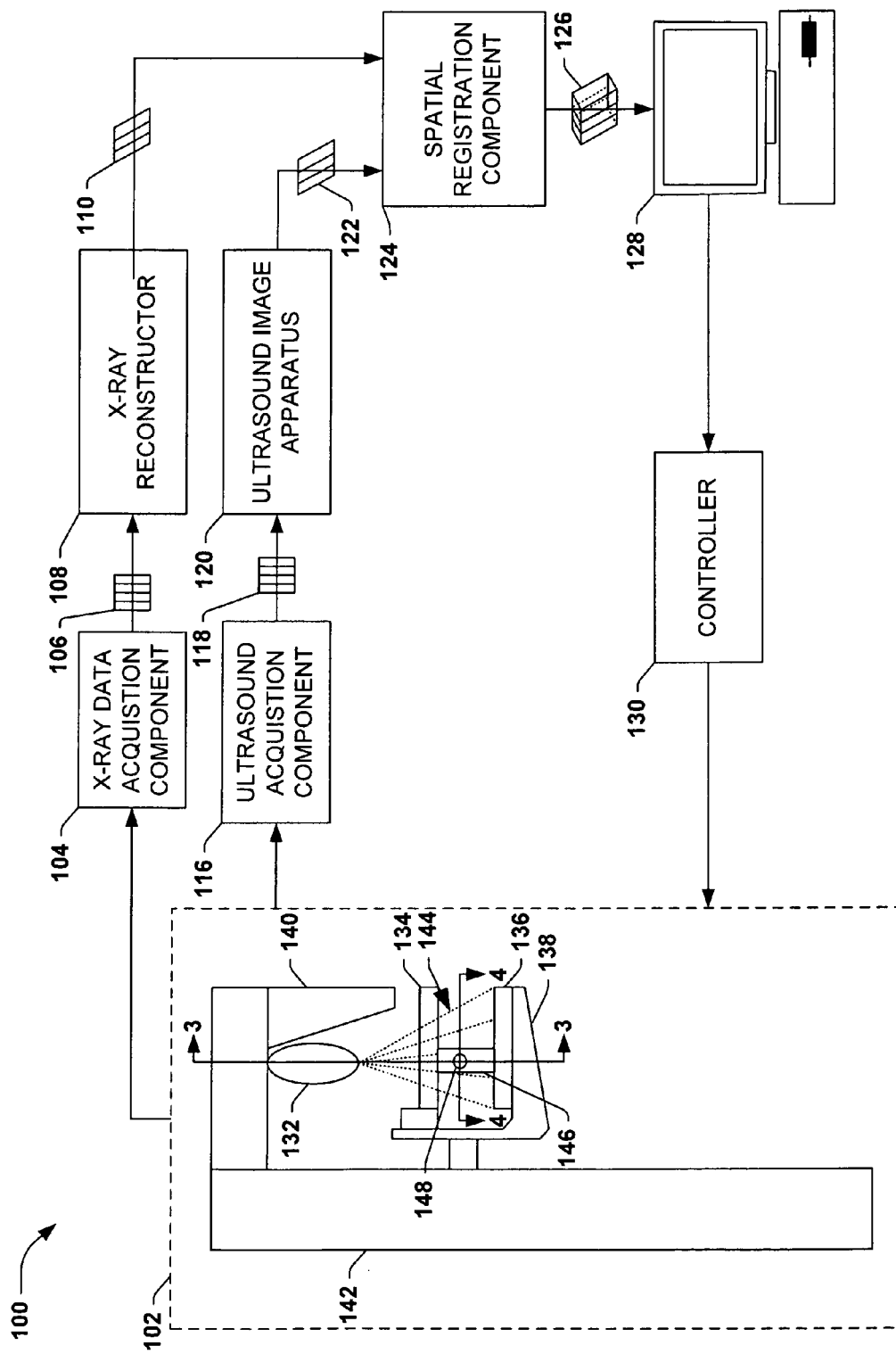
FIG. 1 is a schematic block diagram illustrating a scanner wherein x-ray and ultrasound data may be acquired.

FIG. 1 depicts an example scanner 100. The scanner 100 may be used to scan tissue (e.g., a breast) at a medical center, for example. As illustrated, the scanner 100 typically comprises an object scanning apparatus 102 configured to scan an object (e.g., human tissue). One or more images of the scanned object may be presented on a monitor 128 (that is part of a desktop or laptop computer) for human observation. In this way, targets of the object that are not visible to the naked eye (e.g., cancer cells comprised within breast tissue) may be displayed in the one or more images and, ultimately, may be detected by the human observer.

The object scanning apparatus 102 is configured to scan an object under examination and transmit data related to the scan to other components of the scanner 100. The object scanning apparatus 102 comprises an x-ray source 132 and a detector array 138. The x-ray source 132 is configured to emit fan, cone, wedge, or other shaped x-ray configuration into an examination region 144 of the object scanning apparatus 102.

X-rays that traverse the object under examination (e.g., the object in the examination region 144) are detected by the detector array 138 located on a diametrically opposing side of the object from the x-ray source 132. Targets (e.g., masses, cancer, scar tissue, etc.) within the object (e.g., a breast) may cause various amounts of x-rays to traverse the object (e.g., creating areas of high traversal and areas of low traversal within the object). For example, less radiation may traverse targets with a higher density (relative to densities of other targets in the object). It will be appreciated that the changes in traversal may be used to create x-ray images of targets within the object. For example, if breast tissue is scanned by the object scanning apparatus 102, regions of tightly compacted cells may appear more prominently on an x-ray image than healthy breast cells (which may be virtually invisible).

In one embodiment, the object scanning apparatus 102 is part of a mammography unit and the object scanning apparatus 102 further comprises a top compression paddle 134 and a bottom compression paddle 136. A vertical support stand 142 may provide a means for suspending the compression paddles 134 and 136, the x-ray source 132, and the detector array 138 above the ground. For example, the vertical support may be seven feet tall so that the compression paddles 134 and 136 align with the height of breast tissue when a person is in a standing position. In one example, the compression paddles 134 and 136 are adjustable along the vertical support 142 to adjust for the varying heights of humans, and a shield 140 may protect a person's head from exposure to the x-rays.

In a mammography unit, for example, the examination region 144 may be comprised between the top compression paddle 134 and the bottom compression paddle 136. When the object (e.g., breast tissue) is inserted between the top and bottom compression paddles 134 and 136, the object is compressed (to even out the tissue and hold the tissue still). While the object is under compression, x-rays may be emitted from the x-ray source 132. To mitigate discomfort caused by the compression, the tissue may be compressed for a short period of time (e.g., approximately 10 seconds). X-rays that traverse the breast while it is compressed are detected by the detector array 138 that is located within and/or below the bottom compression paddle 136.

The object scanning apparatus 102 may also comprise an ultrasound component 146. The ultrasound component 146 may be configured to emit a plurality of sound waves, electromagnetic waves, light waves, or other image producing transmission into the examination region 144, and/or detect emitted sound waves, for example, that have interacted with the object, in such a manner that the detected sounds waves can be used to generate an ultrasound image of object that depicts a plane of the object substantially parallel to a plane depicted in an x-ray image of the object. For example, in mammography, a horizontal slice of breast tissue is depicted in an x-ray image, and the ultrasound component 146 may be configured to emit and/or detect sound waves in such a manner that it ultimately causes the resulting ultrasound image(s) to also depict a horizontal slice of breast tissue in a plane substantially parallel to the plane of the x-ray image. In one example, the ultrasound component 146 emits sound waves in a direction substantially perpendicular to a trajectory of a center x-ray beam associated with the x-ray source 132 and/or perpendicular to a detector plane formed by the detector array 138. It will be understood by those skilled in the art that the terms "center x-ray beam" as used herein refers to an x-ray beam that impacts the detector array at a ninety degree angle (e.g., the center beam of a fan, cone, wedge, or other shaped x-ray configuration).

It will be appreciated that the ultrasound component 146 may be configured to detect transmission waves and/or reflection waves depending upon its configuration. In one example, a single transducer 148 of the ultrasound component 146 both emits sound waves and detects those sound waves that have reflected off targets in the object. In another example, one transducer 148 emits sound waves and another transducer, positioned on a diametrically opposing side of the object, detects sound waves that have traversed the object under examination.

It will also be appreciated that the ultrasound component 146 and/or components of the ultrasound component 146 (e.g., one or more transducers 148 comprised within the ultrasound component 146) may be configured to adjust (e.g., vertically) relative to the object to acquire data that may used to create a plurality of images, respective images depicting various parallel planes of the object. In this way, a plurality of ultrasound images may be formed, each ultrasound image of the plurality depicting a scanning of the object that is both substantially parallel to the planes depicted in the other ultrasound images of the plurality of images and substantially parallel to the plane depicted in the x-ray image. In one example, a doctor may take a series of ultrasound images, each depicting a unique slice of the object, for example, and compare it to an x-ray image (e.g., depicting the entire object collapsed or flattened in one plane) to determine what is below, above, and/or to the side of a mass depicted in the x-ray image.

In the example scanner 100, an x-ray data acquisition component 104 is operably coupled to the object scanning apparatus 102 and is configured to collect information and data related to x-rays that were detected by the detector array 138. The x-ray data acquisition component 104 may also be used to compile the collected data (e.g., from multiple perspectives of the object) into one or more x-ray projections 106 of the object.

The illustrated example scanner 100 also comprises an x-ray reconstructor 108 that is operably coupled to the x-ray data acquisition component 104, and is configured to receive the x-ray projections 106 from the x-ray data acquisition component 104 and generate 2-D x-ray image(s) 110 indicative of the scanned object using a suitable analytical, iterative, and/or other reconstruction technique (e.g., backprojection from projection data space to image data). The x-ray image(s) 110 illustrate the latitudinal dimension (e.g., orthogonal to a center x-ray beam and parallel to the detector array) of the object. That is, the images may not depict the vertical height, for example, of a target inside an object when x-rays are emitted from above the object under examination.

The example scanner 100 also comprises an ultrasound acquisition component 116 that is operably coupled to the object scanning apparatus 102 and is configured to collect information and data related to sounds waves that are detected by the ultrasound component 146. The ultrasound acquisition component 116 may also be configured to compile the collected data into projection space data 118. As an example, data from a plurality of transducers positioned about the object may be compiled into projection space data 118.

In the example scanner 100, an ultrasound image apparatus 120 is operably coupled to the ultrasound acquisition component 116, and is configured to receive the projection space data 118 from the ultrasound acquisition component 116 and generate ultrasound image(s) 122. That is, ultrasound image apparatus is configured to convert sound waves into one or more images 122 using techniques known to those skilled in the art (e.g., beam forming techniques). It will be understood to those skilled in the art that the one or more 2-D x-ray images 110 and the one or more ultrasound images 122 depict substantially parallel planes of the object under examination.

In another embodiment, the x-ray source 132 and/or the detector array 138 may be configured to vary their relative position to one another. For example, the x-ray source 132 may be configured to rotate about a portion of the object under examination (e.g., 20 degrees left and right of center). In this way, data from a variety of perspectives (e.g., angles) of the object can be collected from a single scan of the object. The data from the variety of perspectives may be combined or synthesized by the x-ray reconstructor 108 using known digital averaging and/or filtering techniques (e.g., tomosynthesis). Each image 110, for example, may be focused on a scanning plane (e.g., a horizontal slice) of the object, which is parallel to the detector plane, and depicts targets within a particular longitudinal range. In this way, a substantially three-dimensional image of the object under examination may be formed by stacking the two-dimensional images 110.

In another embodiment, the ultrasound component 146 is configured to acquire data from a plurality of angles along a similar scanning plane of the object. In this way, a computed tomography ultrasound (e.g., similar to a computed tomography scan using x-rays) of the object may be acquired, for example. Ultrasound data may be acquired from a plurality of angles by a rotatable ultrasound component and/or an ultrasound component that comprises a plurality of transducers situated about the object (e.g., forming an arc about the object), for example.

It will be appreciated that where the ultrasound component 146 acquires data from a plurality of angles, the ultrasound image apparatus 120 may use more a suitable analytical, iterative, and/or other reconstruction technique (e.g., similar to the techniques used to generate computed tomography images from x-ray data). In one example, the ultrasound image apparatus 120 may also place emphasis on particular types of data generated based upon the detected sound waves (e.g., elastography, reflection, transmission, etc.).

In some instances, the x-ray images 110 and the ultrasound images 122 may be spatially coincident to one another. That is, the plane of the object depicted in at least one x-ray image may correspond to a plane of the object depicted in at least one ultrasound image, in such a way that the ultrasound image may be overlaid onto the x-ray image or vice-versa. For example, if the x-ray images 110 depict five different planes of object (e.g., each plain representing a horizontal slice ⅕ the width of the total object), the ultrasound component and/or components of the ultrasound component may be configured to adjust so as to cause five ultrasound images 122 to be produced. Each of the five ultrasound images 122 produced may have spatial coincidence with one of the x-ray images 110, for example.

The illustrated example scanner 100 further comprises a spatial registration component 124. The spatial registration component 124 is in operable communication with the ultrasound image apparatus 120 and the x-ray reconstructor component 108. The spatial registration component 124 is configured to combine the one or more x-ray images 110 with one or more ultrasound images 122 to form one or more combined images 126 (through the process of fusion) when the x-ray image(s) and the ultrasound image(s) are spatially coincident. That is, the spatial registration component 124 is configured to combine complementary information from two modalities (e.g., an x-ray image 110 and an ultrasound image 122) through suitable analytical techniques (e.g., retrospective registration algorithms, algorithms based on entropy, etc.).

It will be understood to those skilled in the art that other configures and components for a scanner are also contemplated. In one example, a single x-ray image 110 (e.g., depicting a collapsed or flattened representation of the object) and a single ultrasound image 122 (e.g., depicting an un-flattened slice of the object parallel to the flattened x-ray image) is produced from data acquired from the object scanning apparatus 102 and the two images are visually compared (e.g., the x-ray image 110 and the ultrasound image 122 are not combined by the spatial registration component 124). Therefore, the scanner may not comprise a spatial registration component 124, for example.

Figure 2:
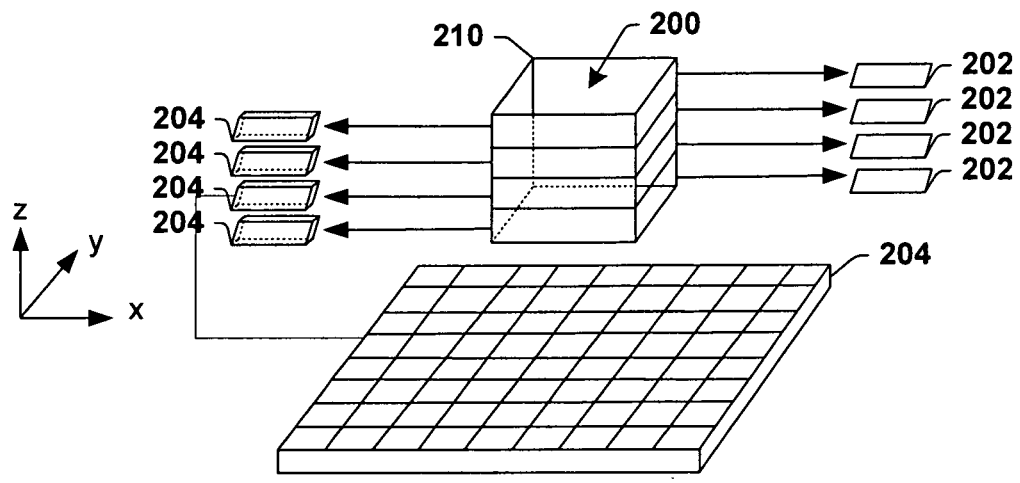
FIG. 2 illustrates example scanning planes of an object that may be acquired.

FIG. 2 illustrates example scanning planes 200 (e.g., horizontal slices) of an object 210 that may be depicted in x-ray images 202 and/or ultrasound images 204. When x-ray data is acquired at a variety of perspectives as discussed above (e.g., an x-ray source is varied with respect to an x-ray detector array) and combined and/or filtered (e.g., using tomosynthesis techniques) x-ray images depicting the illustrated example scanning planes 200 may be produced. It will be appreciated that the x-ray images 202 generally depict the various scanning planes 200 in a flattened latitudinal dimension (e.g., x, y), such that targets in a scanning plane are depicted in the image generally having no discernable z coordinate.

Ultrasound images 204 depicting similar scanning planes 200 to those depicted in the x-ray images may also be produced. The ultrasound images 204 may depict the scanning planes 200 in a flattened latitudinal dimension or in an unflattened latitudinal dimension (e.g., depicting x, y, and z dimensions). The example ultrasound images 204 depict the scanning planes in an unflattened latitudinal dimension. That is, they are depicted as having x, y and z dimensions. Unflattened ultrasound images may be useful to more easily determine the z coordinate of a target in the object (e.g., relative to comparing a plurality of flattened x-ray and/or flattened ultrasound images depicting various scanning planes), for example.

Once x-ray images 202 and ultrasound images 204 are acquired, x-ray and ultrasound image that are spatially coincident may be combined (e.g., by a spatial registration component similar to 124 in FIG. 1) to form a combined image. That is, an x-ray image depicting a particular plane may be combined with an ultrasound image depicting a similar plane to form a combined image. It will be appreciated that while the images may be combined to form combined images, the ultrasound images 204 and the x-ray images 202 may also remain separated and viewed independently (e.g., manually by a physician), for example. It will also be appreciated that the ultrasound images 204 and the x-ray images may not be spatially coincident (e.g., because they depict different planes of the object 210). Nevertheless, they may provide helpful (diagnosis) information, such as the location of a mass/tumor in the x, y and z direction, for example.

Figure 3:
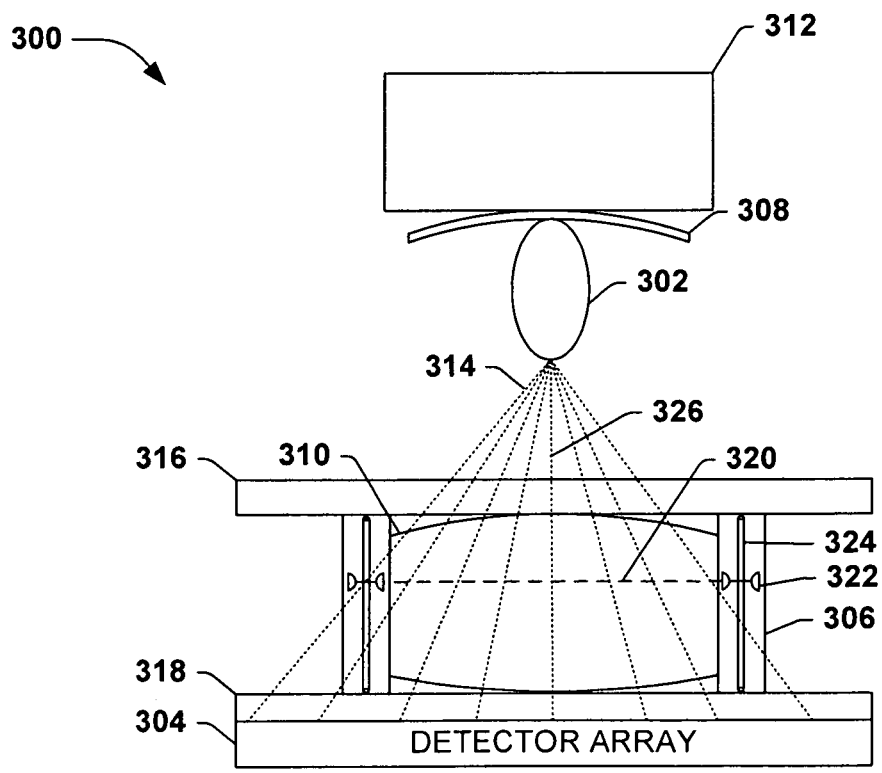
FIG. 3 illustrates a cross-sectional area of an object scanning apparatus wherein x-ray and ultrasound data may be acquired.

FIG. 3 is a cross sectional area (e.g., taken along line 3-3 in FIG. 1) of an example object scanning apparatus 300 (e.g., 102 in FIG. 1). The object scanning apparatus 300 comprises an x-ray source 302 (e.g., 132 in FIG. 1), a detector array 304 (e.g., 138 in FIG. 1), and an ultrasound component 306 (e.g., 146 in FIG. 1). In the illustrated example, the x-ray source 302 is affixed to a guide mechanism 308 that is configured to rotate the x-ray source 302 about a portion of an object 310 under examination (e.g., 20 degrees left and/or right of center). The guide mechanism 308 may be suspended from a vertical support stand 312 (e.g., 142 in FIG. 1). It will be understood to those skilled in the art that the guide mechanism 308 may be unnecessary in certain applications, such as those in which data is not collected from a variety of perspectives, the x-ray source 302 is stationary while the detector array rotates 304, etc.

X-rays 314 are emitted from the x-ray source 302 and traverse the object 310 under examination. X-rays 314 that traverse the object 310 are detected by the detector array 304 positioned on a diametrically opposing side of the object 310 from the x-ray source 302. In the illustrated example, the object 310 (e.g., tissue) is compressed between a top compression paddle 316 and a bottom compression paddle 318 (similar to those used on mammography apparatuses) to condense and/or even out the object (e.g., to promote image quality).

The ultrasound component 306 is configured to send and/or receive sound waves 320 that interact with the object 310. In the example scanning apparatus, the ultrasound component 306 is positioned between the top compression paddle 316 and the bottom compression paddle 318 and is configured to contact the object 310 under examination. Using this configuration (e.g., the ultrasound component 306 perpendicular to the detector array 304 and/or parallel to a center x-ray beam 326), the ultrasound component 306 may acquire data relating to the sound waves while the detector array 304 is acquiring data related to the x-rays since the two modalities occupy different space (e.g., the detector array occupies space below the object 310 and the ultrasound component 306 occupies space to the side of the object 310).

In one example, the ultrasound component 306 is attached to, and movable along, one or both of the compression paddles 316 and 318. That is, one or both of the compression paddles 316 and 318 comprise tracks (e.g., along their horizontal surface) and the ultrasound component 306 slides along the tracks based upon the size of the object 310 under examination, for example, to come into contact with and/or move away from the object 310.

The ultrasound component 306 may comprise one or more transducers 322 (e.g., 148 in FIG. 1). In one example, the transducers 322 are single element transducers (e.g., similar to endo-transducers) that are affixed to a guide mechanism 324. The transducers may rotate about the guide mechanism 324 and/or move vertically along it, for example. In this way, ultrasound scans may be isolated to a particular scanning plane (e.g., horizontal slice) of the object 310 under examination. For example, data that is acquired while the one or more transducers 322 are in the upper elevation of object 310 may relate to the upper vertical portion of the object 310, and data acquired while the one or more transducers 322 are in the lower vertical portion of the object 310 may relate to the lower vertical portion of the object 310. Data acquired from the particular portion of the object 310 that was isolated by the transducers may be reconstructed to form an image, depicting targets comprised in a particular scanning plane of the object 310 which is parallel to the detector array 304 and parallel to a plane depicted in the x-ray image. While the illustrated object scanning apparatus 300 illustrates two transducers 322 (e.g., one on each side of the object 310) it will be understood to those skilled in that art that a different number of transducers 322 may be used. Additionally, the sound waves may be emitted and/or detected from another type of ultrasound mechanism, such as a multi-element probe, for example.

It will be understood to those skilled in the art that the data that is acquired from substantially vertical x-rays 314 may be compiled (e.g., through reconstruction techniques) to form one or more x-ray images (e.g., 110 in FIG. 1) that depict a scanning plane of the object 310, if the position of the x-ray source is rotated relative to the x-ray detector during the scan (e.g., to acquire data from a variety of perspectives of the object). Additionally, the x-ray images may be combined (e.g., fused) with one or more corresponding ultrasound images to form a combined image (e.g., 126 in FIG. 1). In one example, the corresponding ultrasound image is representative of data acquired while the one or more transducers were located in the scanning plane corresponding to the x-ray image.

Figure 4:
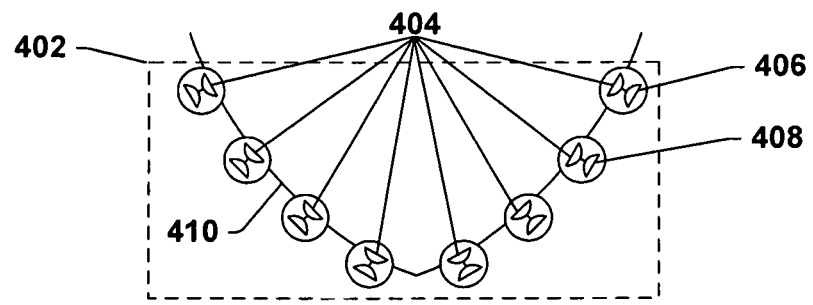
FIG. 4 illustrates a cross-sectional area of an ultrasound component comprising a plurality of transducers.

FIG. 4 illustrates the cross sectional area (e.g., taken along line 4-4 in FIG. 1) of an ultrasound component 402 comprising a plurality of transducers 404 that may be arranged about the object in a particular scanning plane (e.g., to acquire a computed tomography ultrasound image along a plane of the object). A plurality of transducers 404 may be used, for example, to mitigate false positives in ultrasound images and/or improve image quality. In one example, a first transducer 406 of the plurality of transducers 404 may emit a first set of sound waves and the plurality of transducers 406 (e.g., including the first transducer) may listen for and/or detect the first set of sound waves. A second transducer 408 may emit a second set of sound waves once the first set of sound waves is detected, for example. After a predetermined number of transducers has emitted sound waves, for example, the plurality of transducers may reposition themselves along the object 410 (e.g., into or out of the page along a guide mechanism similar to 324 in FIG. 3). In this way, the transducers 404 may detect sound waves that reflect and/or traverse the object 410 under examination, whereas a single transducer may not as thoroughly detect sound waves that traverse the object 410 under examination, for example. Additionally, using a plurality of transducers 404 may minimize artifacts (e.g., white streaks) in an image caused by areas of the object 410 that sound waves did not reach and/or areas where a weak signal was detected (e.g., because the sound waves were reflected off another target within the object).

Data collected from the plurality of transducers 404 while the transducers 404 were in a particular scanning plane of the object 410, for example, may be combined by an ultrasound acquisition component (e.g., 116 of FIG. 1) and/or reconstructed by an ultrasound image apparatus (e.g., 120 in FIG. 1) to form a tomography image of targets within the scanning plane. A second computed tomography image may be acquired based upon data detected while the transducers are in a second scanning plane of the object 410, for example.

These computed tomography images may be combined with x-ray images representing similar planes of the object 410 to form one or more combined images (e.g., 126 in FIG. 1).

Figure 5:
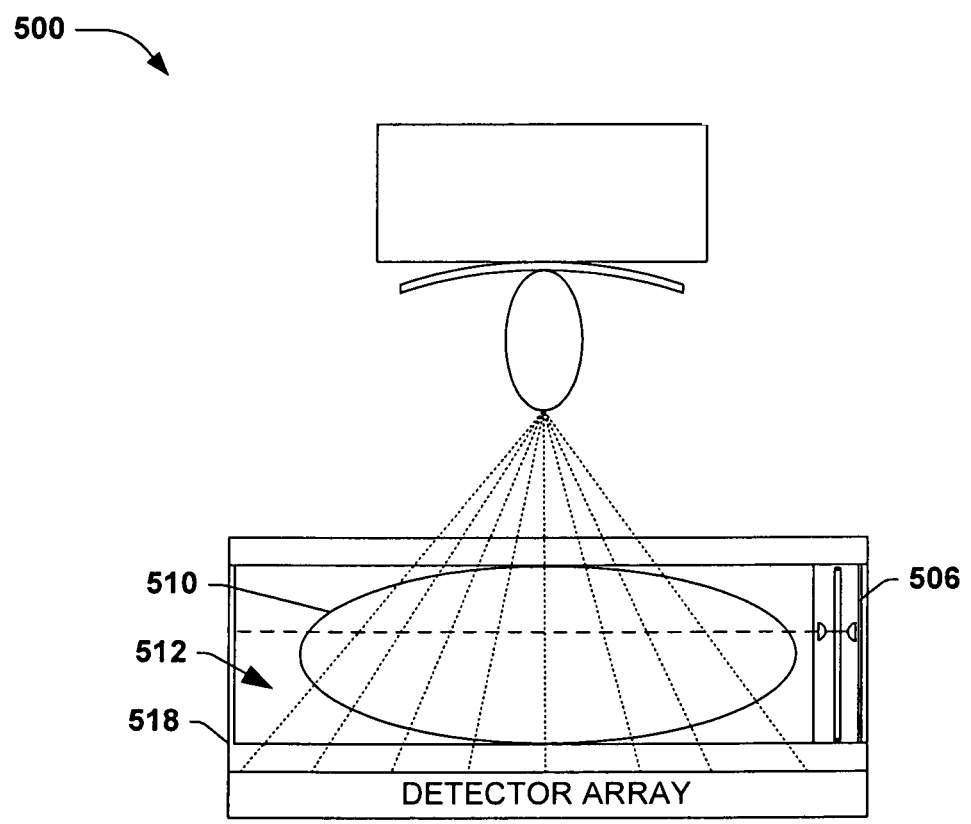
FIG. 5 illustrates a cross-sectional area of an object scanning apparatus wherein x-ray and ultrasound data may be acquired.

FIG. 5 is a cross sectional area (e.g., taken along line 3-3 in FIG. 1) of another example object scanning apparatus 500 (e.g., 102 in FIG. 1). The example scanning apparatus 500 includes an ultrasound component 506, which may operate as set forth in U.S. Patent Application No. 20040030227, bearing Ser. No. 10/440,427 to Littrup et al., the entirety of which is hereby incorporated by reference herein. Unlike object scanning apparatus 300 in FIG. 3, the ultrasound component 506 (e.g., 306 in FIG. 3) may not be in contact with the object 510 (e.g., 310 in FIG. 3 or 410 in FIG. 4) because the object 510 is submersed in a conductive fluid 512 (e.g. water) that allows the sound waves to transfer between the object 510 and the ultrasound component 506. The fluid 512 may be stored in a compression paddle 518 (e.g., 318 in FIG. 3) that has walls configured to mitigate fluid flow outside of the compression paddle 518, and the ultrasound component 506 may be attached to the wall of the compression paddle 518, for example. Additionally, the ultrasound component 506 may be capable of rotating about a scanning plane of the object 510 (e.g., in a circular plane into and out of the page). In this way, a (single) rotatable ultrasound component 506 comprising a single transducer, for example, may provide benefits similar to a plurality of transducers (e.g., 404 in FIG. 1) that are in contact with the object 510. That is, data from a variety of perspectives may be used to produce one or more computed tomography ultrasound images of the object. In some applications, a rotatable ultrasound component 506 may be better than a plurality of transducers attached to the object because less set up time may be necessary for the procedure (e.g., a breast examination) and/or less discomfort since the transducer may not be pressed against the object 510 (e.g., breast tissue) being examined, for example. It will be appreciated that the rotatable ultrasound component 506 and/or portions of the ultrasound component may also traverse various scanning planes of the object (e.g., moving up or down the page) to produce a plurality of images, each image depicting targets in a different scanning plane of the object, for example.

Figure 6:
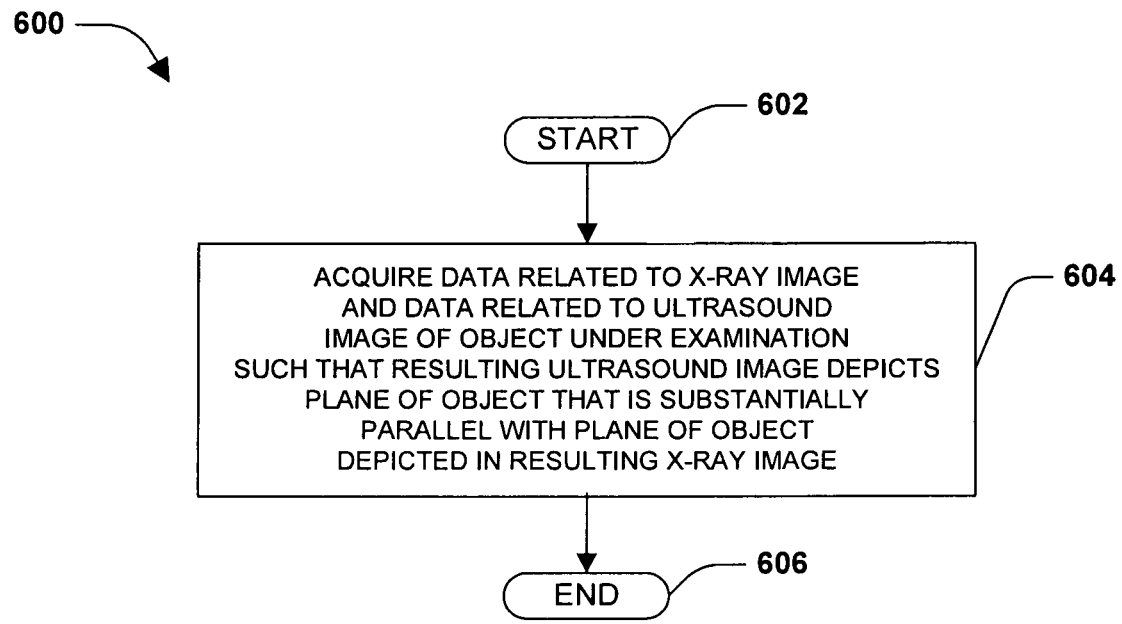
FIG. 6 is a flow diagram illustrating an example method of acquiring data from two scanning modalities.

FIG. 6 illustrates an exemplary method 600 of presenting data acquired from two scanning modalities. The method begins at 602, and data related to an x-ray image and data related to an ultrasound image of the object under examination are acquired such that the ultrasound image depicts a plane of the object that is substantially parallel with a plane of the object depicted in the x-ray image. In one example, the ultrasound image and the x-ray image have spatial coincidence. That is, a plane of at least one x-ray image, created from data acquired by from the x-ray modality, corresponds to a plane of an ultrasound image, created from data acquired by the ultrasound modality, in such a way that the ultrasound image may be overlaid onto the x-ray image or vice-versa.

It will be appreciated that such coincidence is not be attainable with disparate equipment (e.g., separate x-ray and ultrasound acquisition devices). Similarly, such coincidence would likewise not be attainable where the object under examination is repositioned in a combined x-ray and ultrasound acquisition device (e.g., a single device is used, but data acquisition occurs at different times) because the orientation of the object would be, at least, slightly different when the different data is acquired. Nevertheless, while the different modalities (e.g., x-ray and ultrasound) may acquire data concurrently as provided herein, it is not a requisite since the system may maintain the orientation of the object during the examination (e.g., the modalities may scan the object consecutively, while the orientation of the object remains substantially fixed).

X-rays are emitted from an x-ray source and detected on a detector array. In one embodiment, the detector array and x-ray source are on diametrically opposing sides of the object, and the x-rays that are detected by the detector array are those that have traversed the object under examination. Since some targets within the object may be characteristically different from other targets within the object (e.g., have different densities, made of different materials, etc.), varying amounts of x-rays will traverse different portions of the object. Data related to x-rays that are detected by the detector array is reconstructed to form an x-ray image depicting a plane of the object, and targets comprised within the plane.

In one example, the object is x-rayed from a plurality of angles to acquire a plurality of two-dimensional (2-D) images of the object from varying angles, and images corresponding to the respective angles are reconstructed from data related to the detected x-rays. For example, the data may undergo tomosynthesis to produce x-ray images representing various scanning planes of the object under examination. It will be understood to those skilled in the art that the number of images that may be produced may be a function of the number of angles the object is x-rayed from (e.g., two angles may allow two images to be produced).

In one embodiment, ultrasound images are acquired based upon one or more transducers of the ultrasound component that are perpendicular to the detector array and emit and/or receive sound waves that have interacted with the object under examination. To acquire a plurality of slices, the transducers and/or the ultrasound component may be adjusted along a trajectory that is substantially perpendicular to the detector array. For example, the transducers may emit and/or detect sound waves in a first scanning plane of the object to acquire data related to sound waves that interact with the object in the first plane, adjust to a second scanning plane, and emit and/or detect a second set of sound waves to acquire data related to sound waves that interact with the object in the second plane. This process may be repeated for multiple scanning planes along the trajectory. Data from respective planes may be reconstructed to acquire ultrasound images representing various scanning planes of the object under examination (e.g., a first image may depict targets comprised in the first scanning plane, a second image may depict targets comprised in the second scanning plane, etc.).

In one embodiment, a computed tomography ultrasound image can be created using a plurality of transducers positioned within a scanning plane of the object. A plurality of transducers may be useful if the object under examination is dense and/or compressed, for example, to improve the image quality of ultrasound images. In one example, the plurality of transducers is positioned in a predetermined scanning plane about the object, and a first set of sound waves is emitted from a first transducer. One or more of the transducers comprising the plurality may detect the first set of sound waves. Once the first set of sound waves are detected, a second transducer of the plurality may emit a second set of sound waves, and one or more of the plurality may detect the second set of sound waves. This process may be repeated until a predetermined number of transducers emit sound waves. It will be appreciated that the plurality of transducers may also traverse various scanning planes of the object to produce a plurality of computed tomography images, each image depicting a scanning plane of the object.

In another embodiment, the object is submerged in a conductive fluid, and the x-ray images and ultrasound images are acquired while the object is submersed in the fluid. In this way, one or more ultrasound transducers may rotate (e.g., in a horizontal scanning plane) about the object to produce one or more computed tomography ultrasound images. Additionally, due to the presence of the conductive fluid, the transducers do not have to be in contact with the object, thereby reducing the time of the examination and/or that discomfort that may be felt when the transducer is pushed against the object.

As discussed above, one or more x-ray images may be combined with one or more ultrasound images when the ultrasound and x-ray images are spatially coincident using techniques known to those skilled in the art. In this way, images from two different modalities may be combined into a single image. This may provide doctors with additional data, such as what is below and above a mass depicted in an x-ray image, for example, to assist in determining whether a mass is malignant or benign. The method ends at 606.

Figure 7:
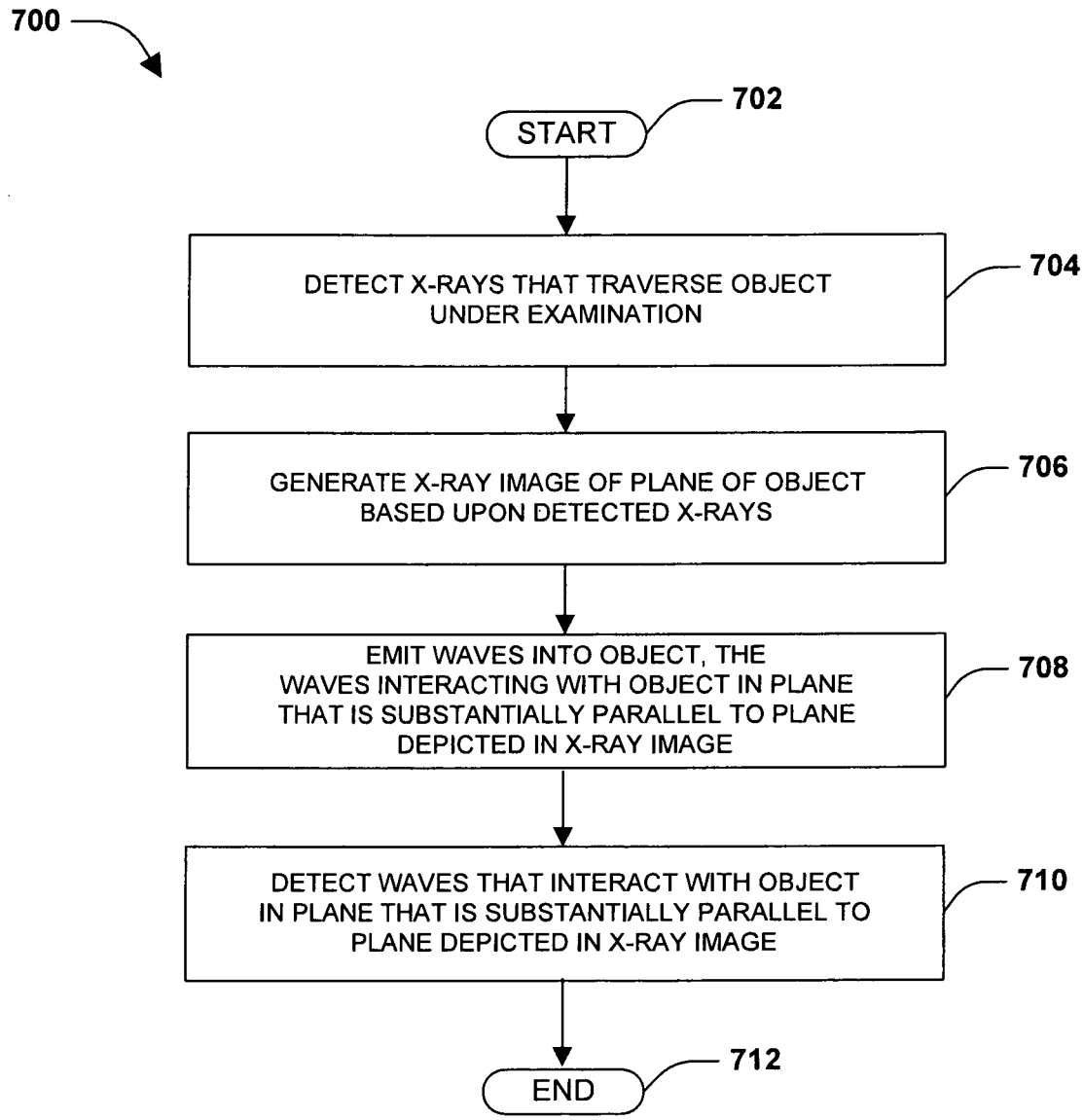
FIG. 7 is a flow diagram illustrating an example method of acquiring data for spatial registration.

FIG. 7 illustrates an example method (700) of spatial registration. The method begins at 702, and x-rays that traverse an object under examination are detected at 704. At 706, an x-ray image of a plane of the object is generated based upon the detected x-rays. In one example, an x-ray source rotates about a portion of the object under examination and x-ray snapshot(s) of the object are taken at predetermined angles. Data from the one or more snapshots may be combined and filtered (e.g., through tomosynthesis) to produce one or more images depicting targets comprised within respective scanning planes (e.g., each image depicts targets in one scanning plane).

At 708, waves are emitted into the object, and the waves interact with the object in a plane that is substantially parallel to the plane depicted in the x-ray image. In one example, sound waves travel through the object in a direction that is substantially perpendicular to a center x-ray beam that was emitted from the x-ray source.

At 710, waves that interact with the object in the plane that is substantially parallel to the plane depicted in the x-ray image are detected. In one example, one or more ultrasound images are produced from the detected waves and are combined with the generated x-ray image (e.g., if they are spatially coincident) using algorithm and/or analytic techniques known to those skilled in the art. The image produced by combining the x-ray image(s) and the ultrasound image(s) may assist a user in detecting of cancer, for example. The method ends at 712.

It will be understood to those skilled in the art that the techniques herein described offer numerous benefits over techniques currently used in the art. For example, since the ultrasound component and the x-ray component produce images in similar planes and both components capture the data while the object has a particular physical position and/or orientation, the information may be more easily fused through coincidence (e.g., alignment) of the planes depicted in the x-ray and ultrasound images. That is, an ultrasound image of a plane of the object can be easily fused with an x-ray image of a similar plane of the object. In some instances, such as where tissue is compressed during the examination, the ability to acquire data from two modalities at once, for example, may reduce the time the tissue is compressed, thereby lessening the duration of the discomfort caused by the compression. Additionally, in the cancer screening, for example, the additional data acquired from using two modalities may reduce the number of false positives in the initial screening and mitigate emotional distress.

The application has been described with reference to various embodiments. Modifications and alterations will occur to others upon reading the application. It is intended that the invention be construed as including all such modifications and alterations, including insofar as they come within the scope of the appended claims and the equivalents thereof. For example, a, an and/or the may include one or more, but generally is not intended to be limited to one or a single item.

What is claimed is:

1. A system, comprising:
    an x-ray source configured to emit x-rays into an examination region within which an object under examination is examined;
    a detector configured to detect at least a portion of the x-rays;
    an ultrasound component configured to emit ultrasound waves into the examination region in a direction substantially perpendicular to a direction in which x-rays are emitted, the ultrasound component operatively coupled to a compression paddle, a surface of the compression paddle which contacts the object laying in a plane extending in an x-direction and a y-direction and the ultrasound component configured for movement within the compression paddle in the x-direction and the y-direction, such that a distance between a trajectory of a center x-ray beam and the ultrasound component is adjustable and such that, at a first time, the ultrasound component contacts the object and, at a second time, the ultrasound component does not contact the object; and
    an ultrasound image apparatus configured to generate an ultrasound image of at least a portion of the object based upon a degree of attenuation experienced by at least some of the ultrasound waves.

2. The system of claim 1, the compression paddle comprising a track and the ultrasound component configured for movement within the track.

3. The system of claim 1, the ultrasound component configured to emit the ultrasound waves concurrently with the x-ray source emitting the x-rays without the ultrasound component x-ray shadowing the object.

4. The system of claim 1, the ultrasound component comprising a transducer configured for movement in a first direction relative to the compression paddle, the first direction substantially perpendicular to the plane.

5. The system of claim 1, the ultrasound component comprising a transducer configured for movement along an axis substantially parallel to the trajectory of the center x-ray beam and configured to emit the ultrasound waves while at specified positions along the axis.

6. The system of claim 5, the ultrasound image representing a first slice of the object generated based upon a degree of attenuation experienced by a first portion of the ultrasound waves corresponding to the transducer being located at a first position along the axis.

* * * * *